US008861812B2

(12) United States Patent
Yoshikawa et al.

(10) Patent No.: US 8,861,812 B2
(45) Date of Patent: Oct. 14, 2014

(54) ULTRASONIC IMAGING APPARATUS

(75) Inventors: Hideki Yoshikawa, Hino (JP); Takashi Azuma, Sagamihara (JP)

(73) Assignee: Hitachi Medical Corporation, Tokyo (JP)

( * ) Notice: Subject to any disclaimer, the term of this patent is extended or adjusted under 35 U.S.C. 154(b) by 750 days.

(21) Appl. No.: 12/866,712

(22) PCT Filed: Feb. 17, 2009

(86) PCT No.: PCT/JP2009/052627
§ 371 (c)(1), (2), (4) Date: Aug. 6, 2010

(87) PCT Pub. No.: WO2009/110308
PCT Pub. Date: Sep. 11, 2009

(65) Prior Publication Data
US 2011/0075904 A1    Mar. 31, 2011

(30) Foreign Application Priority Data
Mar. 7, 2008   (JP) ................................. 2008-057167

(51) Int. Cl.
*A61B 8/00*   (2006.01)
*A61B 8/14*   (2006.01)
*A61B 8/06*   (2006.01)
*G01S 7/52*   (2006.01)

(52) U.S. Cl.
CPC ............... *A61B 8/06* (2013.01); *G01S 7/52071* (2013.01); *G01S 7/52033* (2013.01); *G01S 7/52074* (2013.01)
USPC .................................. 382/128; 705/2; 705/3

(58) Field of Classification Search
USPC ....................................................... 382/128
See application file for complete search history.

(56) References Cited

U.S. PATENT DOCUMENTS

| 6,760,486 | B1 * | 7/2004 | Chiao et al. ................... 382/274 |
| 7,024,024 | B1 | 4/2006 | Aiazian |
| 2005/0059893 | A1 * | 3/2005 | Ogasawara et al. ........... 600/454 |
| 2009/0048516 | A1 | 2/2009 | Yoshikawa et al. |
| 2009/0299182 | A1 * | 12/2009 | Asafusa ....................... 600/443 |

FOREIGN PATENT DOCUMENTS

| CN | 1593348 | 3/2005 |
| EP | 1 514 516 | 3/2005 |
| EP | 1 884 197 | 2/2008 |

(Continued)

OTHER PUBLICATIONS

European Search Report for European Patent Application No. 09716554.2, issued on Nov. 12, 2012.

*Primary Examiner* — Hiep V Nguyen
(74) *Attorney, Agent, or Firm* — Antonelli, Terry, Stout & Kraus, LLP.

(57) ABSTRACT

Provided is an ultrasonic imaging apparatus including: a time-gain controller (TGC) that compensates an amplitude fading occurring in the process of propagation inside a living body; a scan converter (SC) that constructs image data; a TIC measurement unit that measures a TIC of each pixel; an evaluation index input unit that inputs an index for evaluating hemodynamics on the basis of a TIC; a mapping parameter estimation unit that estimates a mapping parameter comparable to an evaluation index; a TIC image construction unit that constructs a two-dimensional image on the basis of the mapping parameter; and a pixel detection unit that extracts a region corresponding to a color map from a TIC image, and utilizing a TIC measured with each pixel so as to measure a difference in hemodynamics.

15 Claims, 12 Drawing Sheets

(56) References Cited

FOREIGN PATENT DOCUMENTS

| | | |
|---|---|---|
| JP | 08-252253 | 10/1996 |
| JP | 2001-054520 | 2/2001 |
| JP | 2005-081073 | 3/2005 |
| WO | WO 2006/123742 | 11/2006 |

* cited by examiner

FIG. 6
(a): TIC OF PIXEL (x,y): $I = I_{max}(1-\exp(-\beta t))$
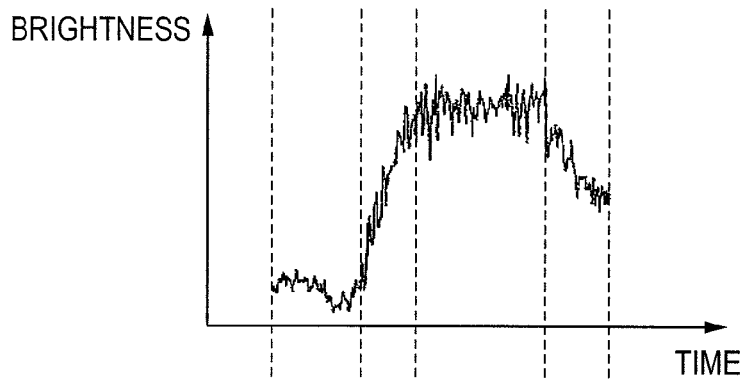
(b): OUTLINE OF TIC
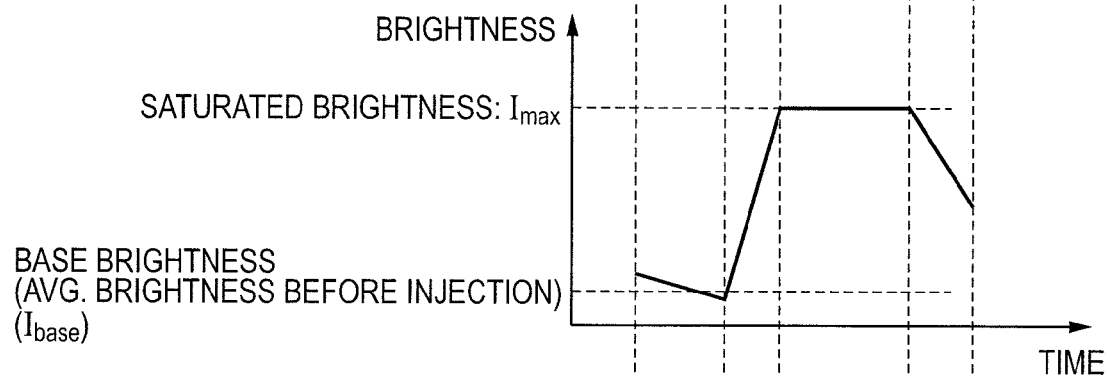
(c): TEMPORAL DIFFERENTIAL OF OUTLINED TIC
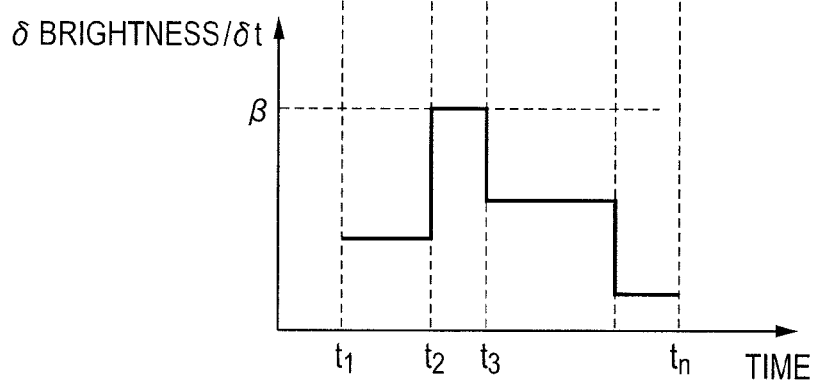

ULTRASONIC IMAGING APPARATUS

INCORPORATION BY REFERENCE

The present application claims the priority of Japanese Patent Application No. 2008-057167 filed on Mar. 7, 2008, the contents of which are incorporated herein by reference.

TECHNICAL FIELD

The present invention relates to a technology for transmitting or receiving ultrasonic waves to or from the inside of a living body, and visualizing the inside thereof, in particular, to an ultrasonic imaging apparatus that performs imaging by utilizing a brightness change in an in vivo tissue due to a contrast medium.

BACKGROUND ART

An ultrasonic imaging apparatus that transmits pulsating ultrasonic waves to the inside of a living body and visualizing internal information on the living body using a receiving signal has the features of a compact apparatus and real-time image display, and is one of imaging apparatuses used versatilely in the field of medicine along with X ray and MRI.

Vascular contrast enhancement is generally known as a technique of obtaining an image in which a vascular network including microscopic structures is highlighted at a higher contrast than peripheral tissues are, and versatilely utilized in each imaging apparatus in clinical practice.

Used as an ultrasonic contrast medium are microscopic bubbles (micro-bubbles) of several micrometers in diameter. A reason why the microscopic bubbles are used lies in that the bubbles resonate with ultrasonic waves of several megahertz employed in a medical field, and bring about scattering waves in a frequency band equivalent to that of a transmitting/receiving pulsating signal. Contrast enhancement based on ultrasonic waves has such features that a contrast medium itself lacks both toxicity and critical invasiveness such as exposure, and that permits real-time observation of a contract-enhanced vessel, though, compared with other imaging apparatuses, a viewing field and a region capable of being imaged are limited.

DISCLOSURE OF THE INVENTION

Problems to be Solved by the Invention

Conventional ultrasonic contrast media are to enhance a contrast-enhancement signal by crushing bubbles through high-sound pressure irradiation. Since an image is acquired by extinguishing the bubbles on an imaging plane, there is a problem that a time during which the same section can be imaged is limited to several seconds. In other words, it is necessary to irradiate ultrasonic waves with a tissue filled with a contrast medium, and to construct an image with a signal acquired during several seconds during which the bubbles are extinguished. In contrast, a contrast medium that has been newly approved in recent years is intended to enhance a contrast-enhancement signal by vibrating bubbles through low-sound pressure irradiation. Since the bubbles on the imaging plane do not vanish, continuous imaging of the same section that has been hard to do with an existing contrast medium can be achieved. Accordingly, the practicality of ultrasonic contrast enhancement diagnosis has drastically improved. In addition, advancement of the contrast enhancement diagnosis having temporal information introduced into a contrast-enhanced image is expected.

One of objects for which contrast enhancement diagnosis proves effective is the liver. Phagocytes called Kupffer cells exist in the normal liver, and work to ingest a contrast medium in blood while regarding the contrast medium as a foreign invader. Owing to the phagocytosis of the Kupffer cells, the normal liver appears with high brightness in a contrast-enhanced image. An abnormal region devoid of the Kupffer cells, such as, a tumor appears with lower brightness than a normal region because the contrast medium is not ingested by the abnormal region. The abnormal region can therefor be rendered at a high contrast ratio.

Aside from a contrast-enhanced image obtained by utilizing the property of Kupffer cells, what is important to distinguish a hepatic tumor is to render a neoplastic vessel. The neoplastic vessel is enhanced with a contrast medium in order to observe the structure or density, whereby information necessary to detect a tumorous tissue embedded in a normal tissue or distinguish a tumor can be obtained. In particular, contrast enhancement observation of an arterial vessel proves effective in distinguishing a hepatocellular carcinoma, and is adopted as a test item mandatory to diagnosis.

However, the liver has the hepatic artery as well as the porta hepatis through which blood having passed through the small intestine flows. It is hard to accurately discriminate the hepatic artery and porta hepatis from each other in a contrast-enhanced image. A technology for discriminating hemodynamics by utilizing a temporal change (time-intensity curve (TIC)) in brightness in an image that varies depending on the concentration of a contrast medium has attracted attention. An intravenously administered contrast medium contrast-enhances the hepatic artery (artery phase) into which blood directly flows from the heart, the porta hepatis through which blood having passed through the small intestine flows, and a tissue (tissue phase), which contains Kupffer cells, in that order. Different TIC shapes are demonstrated in the respective contrast-enhancement phases. Therefore, a vessel in the artery phase is expected to be identified based on the results of TIC measurement. Presentation of an image containing information equivalent to information provided by CT angiography (CTA) that is currently most frequently utilized for the same purpose is expected.

For example, a technology described in patent document 1 is such that: the relationship of association between a value of information to be displayed and a brightness or color on a screen is indicated with a color bar; and a display range is optimized by referencing the relationship of association.

Patent document 2 describes that patterns of a brightness change typical to a noise, which is a pixel representing a brightness change which varies irregularly among low brightness levels, or a living-body signal are prepared in advance, and that the brightness change of a measured pixel is compared with the patterns in order to identify the source of the signal in the region.

As mentioned above, since visualization of hemodynamics provides information important to distinguish a tumor, a need therefor in clinical practice is high. In addition, utilization of a TIC is effective in visualizing a blood vessel especially in a specific contrast-enhancement phase. The advent of a novel contrast medium that permits contrast enhancement without being extinguished is quite consistent with high-precision measurement of a TIC.

Hemodynamics in each contrast-enhancement phase is very complex. In particular, the hemodynamics in an artery phase and that in a portal vein phase exhibit similar tendencies. Therefore, it is hard to determine an evaluation index for use in identifying the hemodynamics from a specific TIC. When a two-dimensional image is differently colored according to the evaluation index, it is hard to designate an optimal range from the two-dimensional image.

When an attempt is made to trace a source of a signal by utilizing a brightness change in a pixel, it is hard to identify hemodynamics that makes it necessary to compare a relative time difference of occurrence of the brightness change with another.

An object of the present invention is to provide an ultrasonic imaging apparatus that performs pixel by pixel measurement of a mapping parameter of hemodynamics based on TIC measurement, and displays a vessel in a contrast-enhancement phase, which an operator selects, on the basis of the mapping parameter.

Patent document 1: Japanese Patent Application Laid-Open Publication No. 2005-81073

Patent document 2: Japanese Patent Application Laid-Open Publication No. 08-252253

Means of Solving the Problems

As an example, the present invention includes: a transducer that transmits or receives ultrasonic waves to or from a subject; an image data production unit that produces plural image data items on the basis of plural receiving signals due to the transducer; a frame memory that preserves the image data items; a temporal change measurement unit that measures a temporal change in brightness of each pixel of image data; an image construction unit that constructs a color map on the basis of the results of the measurement by the temporal change measurement unit; an input unit that inputs display item information concerning the color map; and a pixel detection unit that extracts pixels from the color map and constructs an extractive image.

Effects of the Invention

According to the present invention, a difference in hemodynamics can be visualized, and a vessel in a contrast-enhancement phase necessary to diagnosis can be specifically displayed.

Another object of the present invention, and features and an advantage thereof will be apparent from a description of an embodiment of the present invention made below in conjunction with appended drawings.

BRIEF DESCRIPTION OF THE DRAWINGS

FIG. 6 is an explanatory diagram concerning a measurement technique for a mapping parameter, which serves as an evaluation index, based on a TIC in accordance with the embodiment 1.

Figure 1:
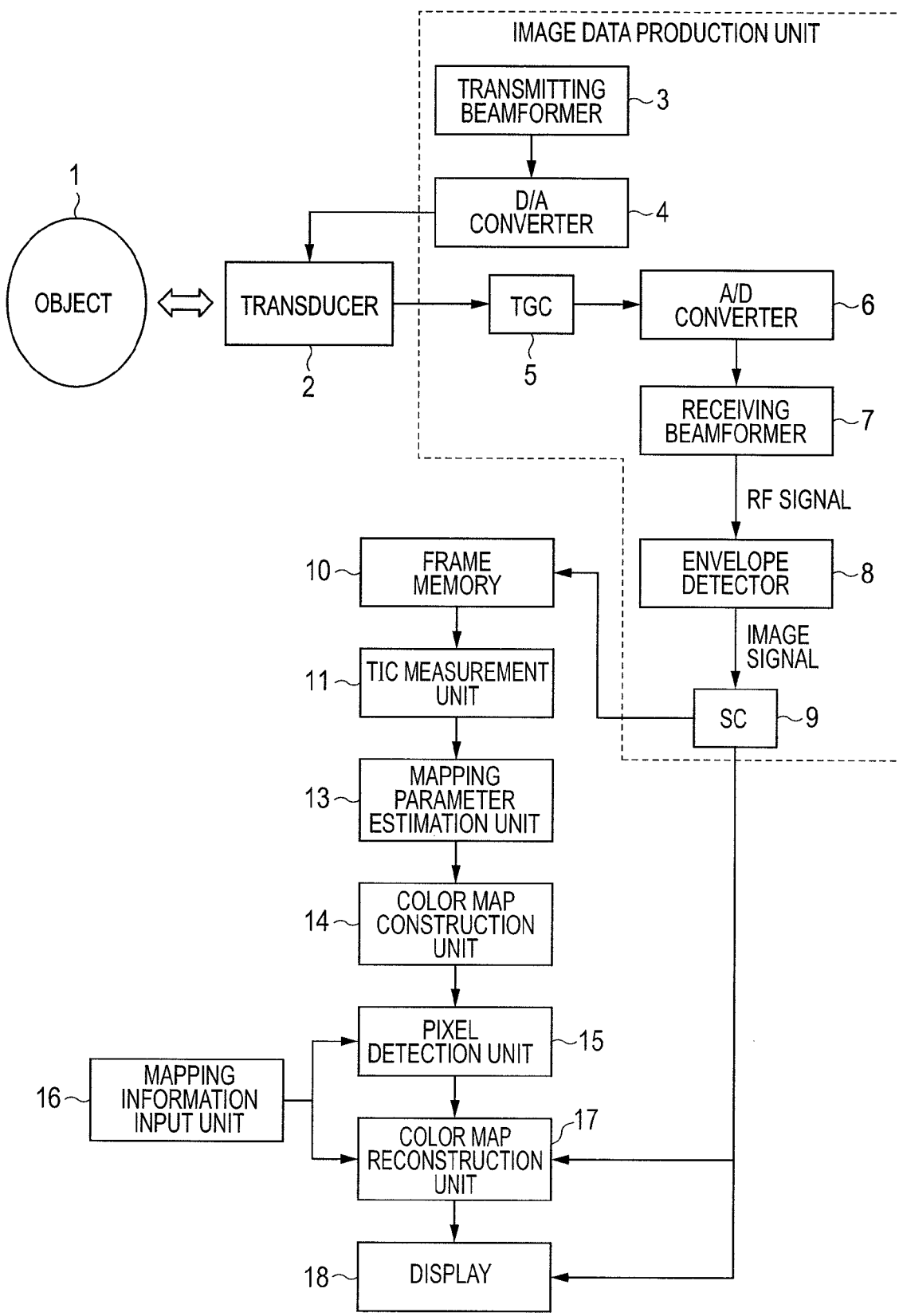
FIG. 1 is a block diagram showing an example of the constitution of an embodiment 1.

DESCRIPTION OF REFERENCE NUMERALS 1 object
2 transducer
3 transmitting beam former
4 D/A converter
5 TGC
6 A/D converter
7 receiving beam former
8 envelope detector
9 scan converter
10 frame memory
11 TIC measurement unit
13 mapping parameter estimation unit
14 color map construction unit
15 pixel detection unit
16 input unit
17 color map reconstruction unit
18 display
32 pixel $(x,y,t_1)$
34 pixel $(x,y,t_2)$
36 pixel $(x,y,t_n)$
41 motion correction unit
81 color map
82 porta hepatis
83 hepatic artery
84 color bar
85 extractive image
91 image data
92 example 1 of a fusion image
101 example 2 of a fusion image
111 TIC display
112 frequency distribution table

BEST MODE FOR CARRYING OUT THE INVENTION

An embodiment of the present invention will be described below in conjunction with the drawings.

Embodiment 1

FIG. 1 is a block diagram showing a constitution of an ultrasonic imaging apparatus in accordance with an embodiment 1 of the present invention.

The ultrasonic imaging apparatus includes: a transducer 2 that transmits or receives ultrasonic waves to or from an object 1; a transmitting beam former 3 and a receiving beam former 7 that give a predetermined time delay, during which a predetermined transmitting/receiving beam is formed, to piezoelectric elements constituting the transducer 2; an analog-to-digital (A/D) converter 6 that analog-to-digital converts a transmitting/receiving signal, and a digital-to-analog (D/A) converter 4; a TGC 5 that compensates an amplitude fading occurring in the process of propagation through the inside of a living body; an envelope detector 8 that detects a received radiofrequency signal and converts it into an image signal; a scan converter 9 that constructs a two-dimensional image from the image signal; a frame memory 10 that preserves the acquired two-dimensional image; a TIC measurement unit 11 (temporal change measurement unit) that measures a TIC of each pixel from preserved image data; a mapping parameter estimation unit (measured value calculation unit) 13 that measures and calculates a value, which serves as an evaluation index for evaluating hemodynamics, on the basis of the measured TIC; a color map construction unit (image construction unit) 14 that constructs a two-dimensional image on the basis of the mapping parameter measured with each pixel; a mapping information input unit (input unit) 16 that inputs information concerning a display item of a noted object or a display format; a pixel detection unit 15 that extracts a region, which is associated with the inputted mapping parameter, from a TIC image; a color map reconstruction unit 17 that reconstructs an image in the inputted display format; and a display 18 that displays the reconstructed image.

Herein, production of image data will be briefly described. An ultrasonic irradiation side of the transducer 2 has plural piezoelectric elements arrayed in a row, and each of the elements fills the role of transmitting or receiving an ultrasonic wave. A voltage pulse from the transmitting beam former 3 is inputted to each of the piezoelectric elements via the D/A converter 4, and an ultrasonic wave is irradiated to the object due to piezoelectric oscillation of the element. At this time, a predetermined time delay is electronically given to the piezoelectric elements, and ultrasonic waves transmitted from the respective piezoelectric elements are focused on a predetermined position inside the object 1. Reflected echoes from the object 1 are received by the respective piezoelectric elements, and the TGC 5 performs amplitude correction according to a propagation distance so as to compensate a fading of a signal occurring in the process of propagation. Thereafter, receiving signals are sent to the receiving beam former 7 via the A/D converter 6, and multiplied by a delay time proportional to a distance from the focal position to each of the piezoelectric element. A result of addition is then outputted (phasing and addition). The ultrasonic transmission/reception is performed on all scan lines along the array of piezoelectric elements, whereby a two-dimensional reflected-echo distribution of the object 1 is obtained. A radiofrequency signal separated into a real part and an imaginary part is outputted from the receiving beam former 7, and sent to the envelope detector 8. The signal sent to the envelope detector 8 is converted into a video signal, and then subjected to inter-scan line pixel interpolation by the scan converter 9. After the signal is reconstructed into two-dimensional image data, the image data is displayed on the display 18.

In the TIC measurement unit 11, during TIC measurement, the processing time can be shortened by reading image data from the frame memory 10 at certain sampling intervals. In principle, if three or more image data items are present within the time (several seconds) of an artery phase, the outline of a TIC can be identified as a curve. Therefore, assuming that n (>3) image data items are preserved during the artery phase of, for example, t sec long, a sampling interval can be set to n/t.

Figure 2:
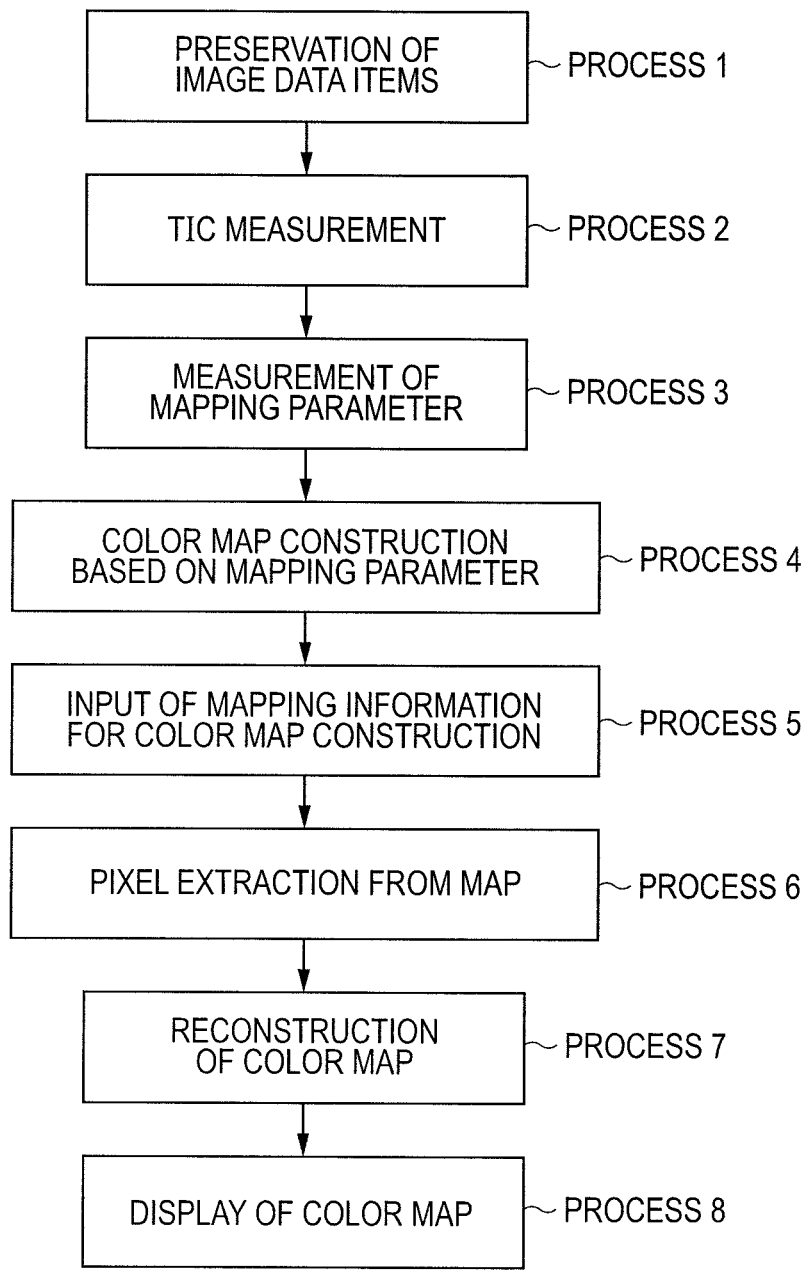
FIG. 2 shows processes, which begin with preservation of image data and end with construction of a hemodynamic image, in accordance with the embodiment 1.

Processing ending with reconstruction of a color map, which represents hemodynamics, from image data preserved in the frame memory 10 will be described based on the constitution of FIG. 1. FIG. 2 shows actual processes.

Figure 3:
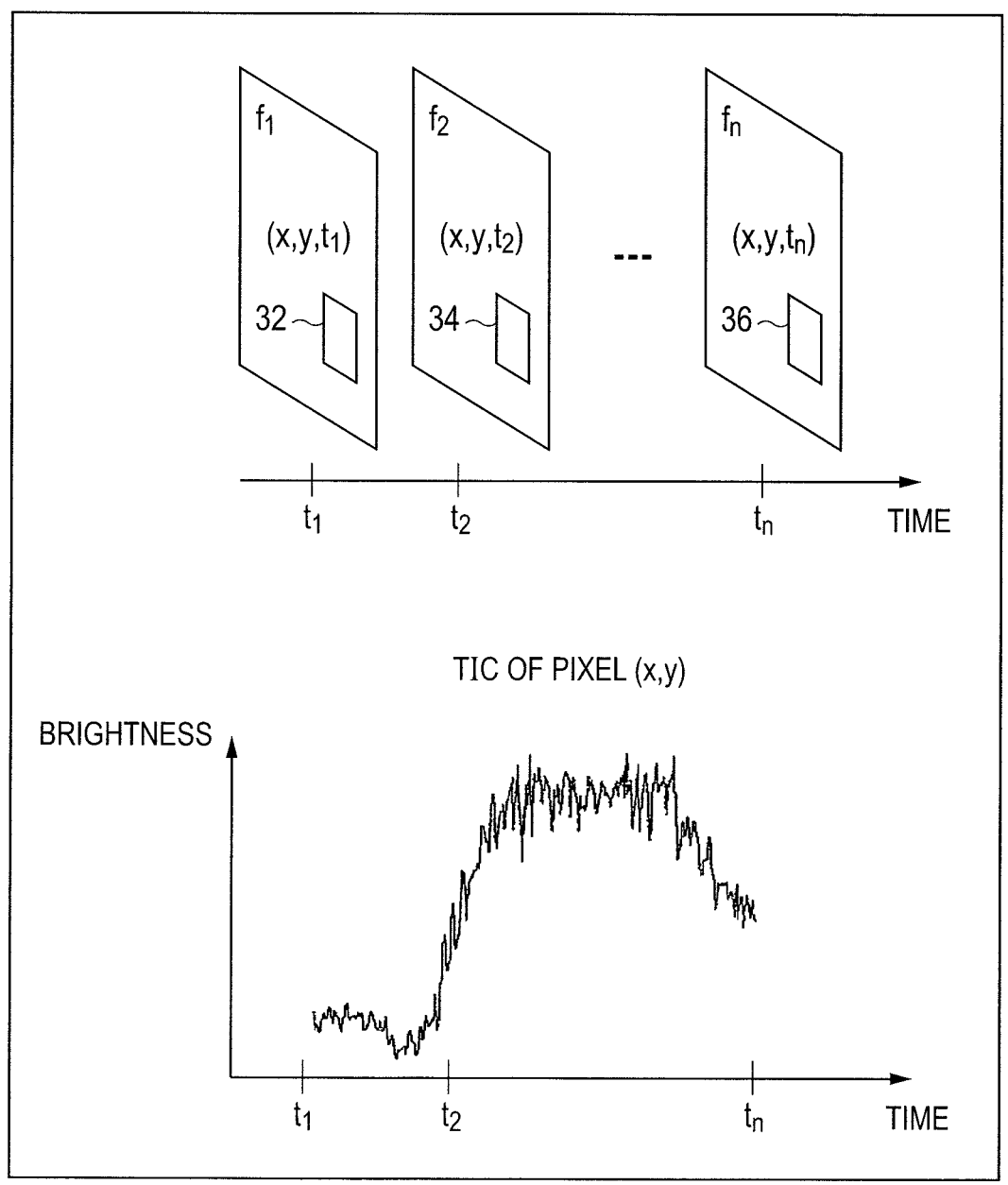
FIG. 3 is an explanatory diagram concerning TIC measurement of a specific pixel in accordance with the embodiment 1.

After image data items representing primarily introduction of a contrast medium and finally filling of a tissue with the contrast medium are preserved in the frame memory (process 1), a TIC of a pixel is measured in process 2. Herein, the TIC of every pixel may be measured or the preserved time-sequential image data items may be displayed on the display 18. When an operator limits an object range for pieces of processing of successive steps including TIC measurement by designating a range, in which the operator is interested, through the input unit, the processing time can be shorted. Image data from the scan converter 9 may be displayed on the display 18 at any time. The operator may originate a trigger using a button on a screen or a panel, which is the input unit, at appropriate timing preceding or succeeding inflow of the contrast medium so as to limit image data items to be preserved in the frame memory 10. When a brightness change in an entire image is noted, a measurement region is automatically limited. For example, assuming that an artery phase is of interest, TICs of all pixels are measured in an initial state, and the results of the measurement are added up for each time phase. A result of the addition keeps growing during the artery phase, and the growth rate decreases towards the second half of the artery phase. The time is used as a threshold, and only pixels whose TICs show a growing tendency are extracted or continuously measured. Thus, a region for TIC measurement can be automatically confined to a region of interest. According to this technique, since the timing at which the result of the addition begins growing, that is, the timing at which the contrast medium begins flowing in can be identified, a frame with which the artery phase begins can be readily specified. As for TIC measurement, when an effect of a body motion is limited, a brightness value of a pixel at the same position in each of images is measured, and the measured values are time-sequentially arrayed. Thus, TIC measurement on the position is readily achieved. For example, as shown in FIG. 3, assuming that image data items acquired from a time instant $t_1$ to a time instant $t_n$ are time-sequentially assigned $f_1$, $f_2$, and $f_n$, and that TIC measurement of a pixel 32 (x,y,$t_1$) in the image data $f_1$ is carried out, brightness values of pixels 34 (x,y,$t_2$) and 36 (x,y,$t_n$) having the same coordinates in the image data items $f_2$ and $f_n$ respectively are measured.

Figure 4:
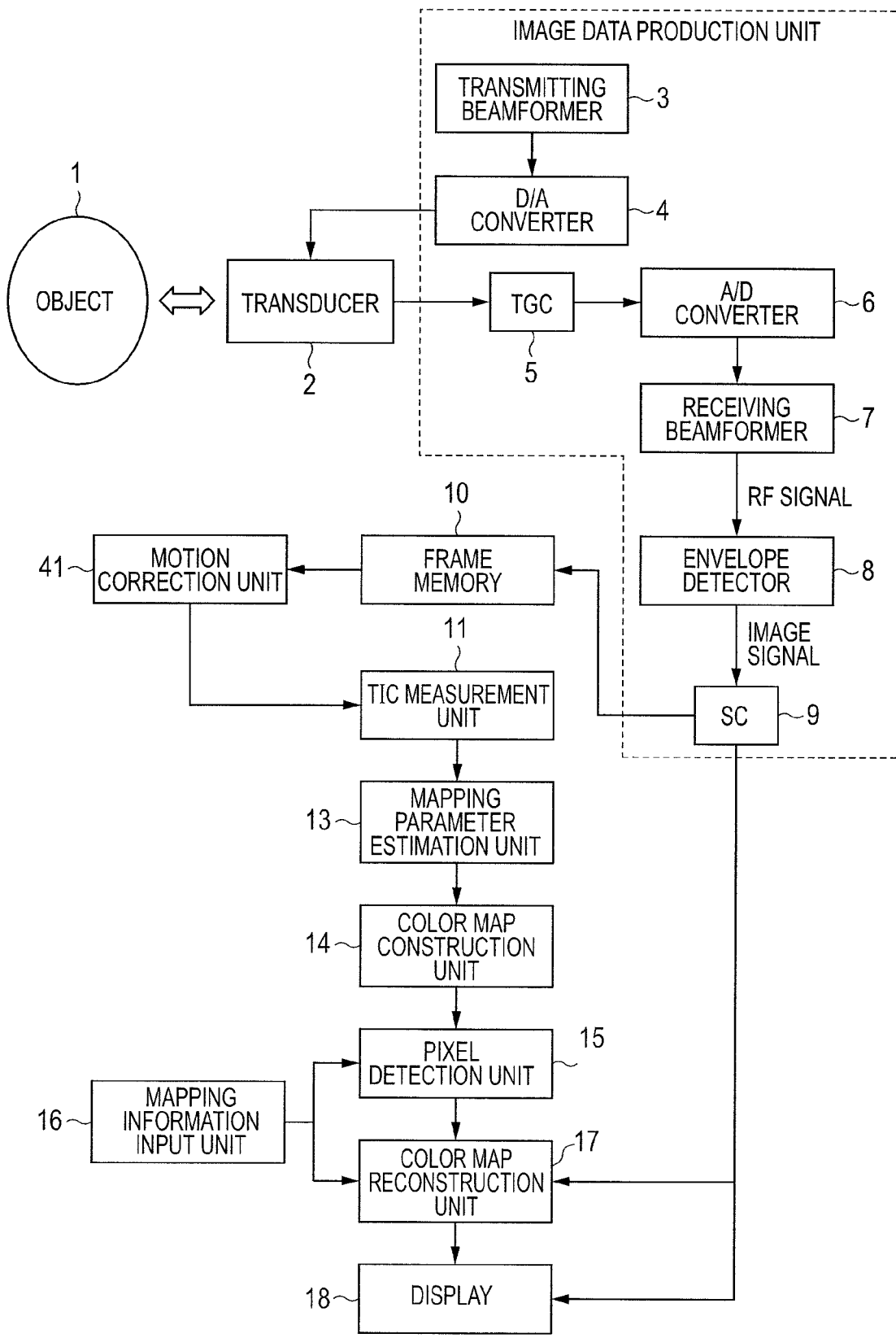
FIG. 4 is a block diagram showing an example of a constitution of the embodiment 1 including a motion correction unit.

When an effect of a body motion is significant, a motion correction unit 41 has to be, as shown in a block diagram of FIG. 4, interposed between the frame memory 10 and TIC measurement unit 11 so as to compensate a body motion occurring over frames. Various methods are conceivable as a body-motion compensation technique. As the easiest method, an image that serves as a reference for compensation processing is selected from among a group of time-sequential images employed in TIC measurement, and typical pattern matching processing such as least squares fitting or cross-correlation arithmetic is employed. Otherwise, compensation processing may be performed on image data items sampled from the group of images at regular intervals, and an overall motion may be estimated based on the results of the processing. In this case, the processing time can be shortened.

Figure 5:
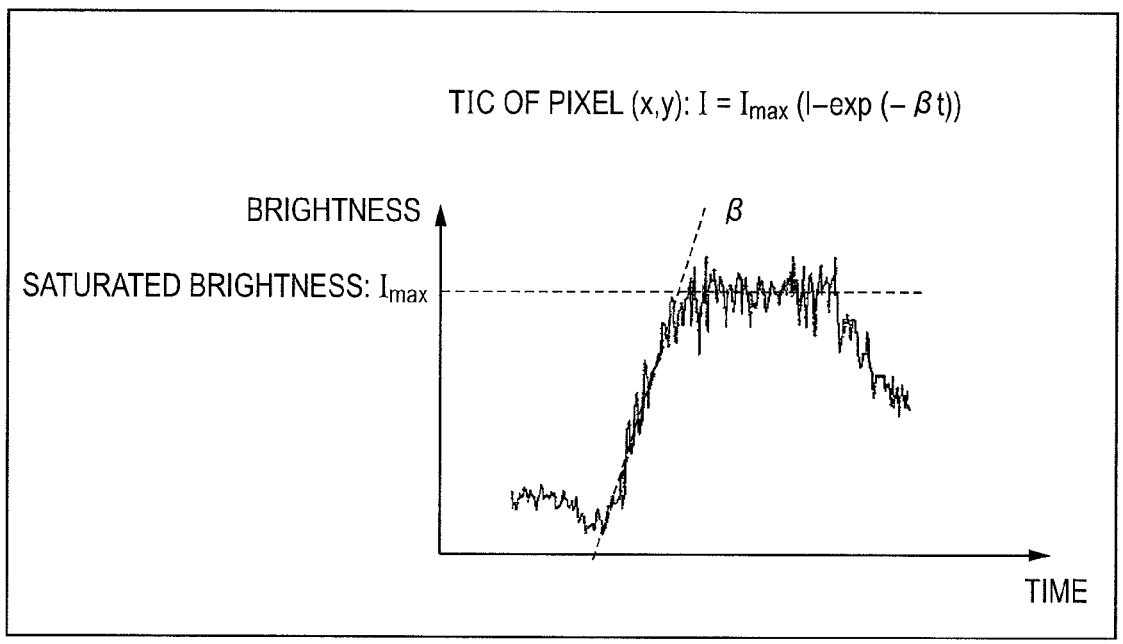
FIG. 5 shows a typical example of a TIC measured with each pixel according to the embodiment 1.

In process 3, the mapping parameter estimation unit 13 estimates a value (mapping parameter) serving as an evaluation index for hemodynamics. When a temporal change (t) in brightness (I) caused by a contrast medium, that is, a TIC is expressed with an equation, the equation is $I=I_{max}(1-\exp(-\beta t))$. Herein, $I_{max}$ denotes a saturated brightness value attained when the flow rate of the contrast medium is saturated, and β denotes a value representing an acceleration of a contrast medium inflow rate (FIG. 5). At least either of a characteristic value of a TIC or a specific change time ($t_{TIC}$) of a temporal change at which a characteristic change occurs is adopted as a mapping parameter.

(a) of FIG. 6 shows a typical example of a TIC measured with each pixel. For the TIC, the mapping parameter estimation unit 13 forms a TIC outline ((b) of FIG. 6) in which the slope of the TIC is simplified using a low-pass filter or sampling processing. On this stage, the saturated brightness value $I_{max}$ and an average brightness before injection $I_{base}$ are measured. Further, the acceleration β of the flow rate of a contrast medium is measured through temporal differentiation (δ(brightness)/δt) of the TIC outline ((c) of FIG. 6).

Figure 7:
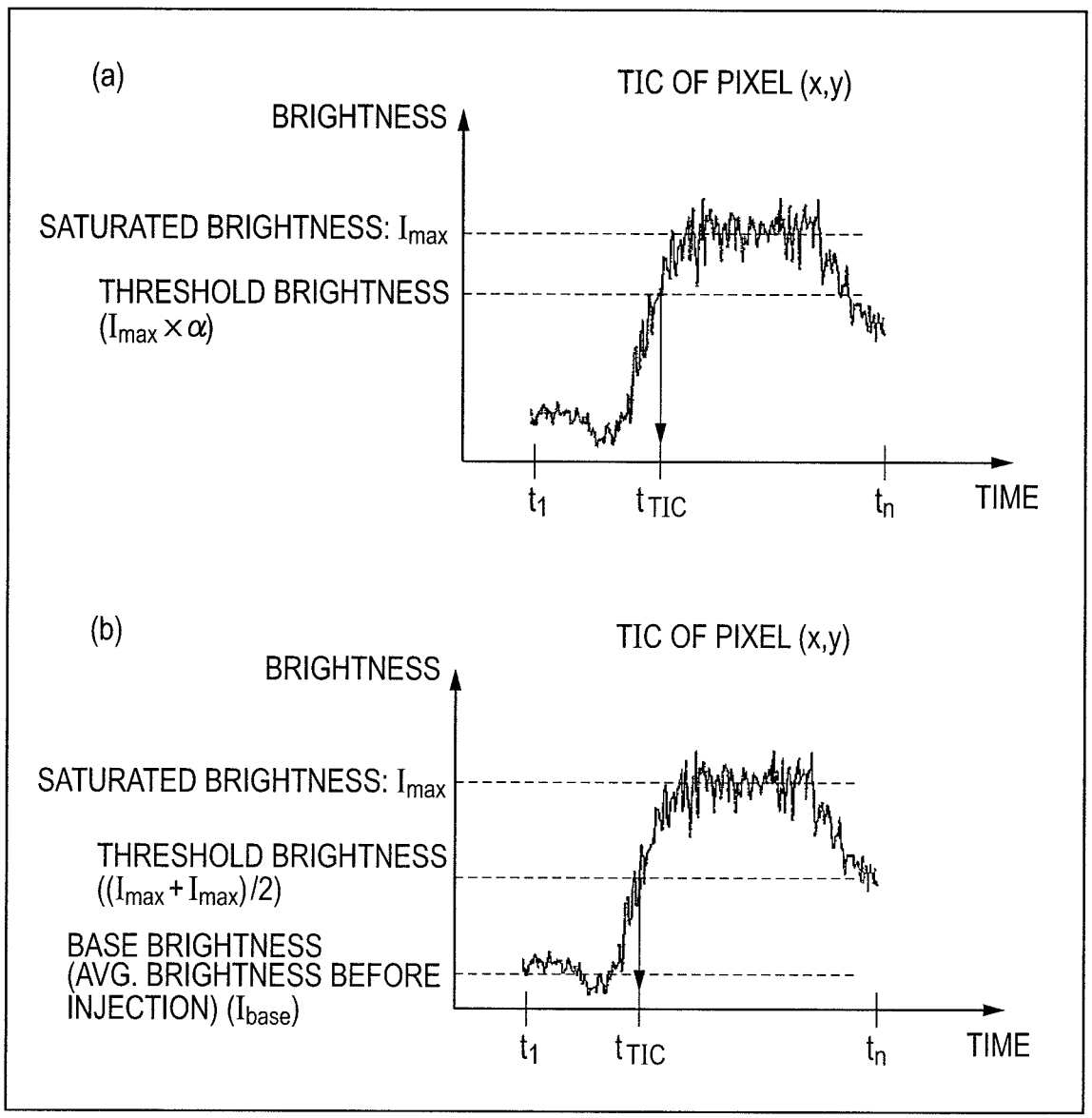
FIG. 7 is an explanatory diagram concerning a measurement technique for threshold brightness based on a TIC in accordance with the embodiment 1.

Herein, $t_{TIC}$ denotes a specific change time of a temporal change, that is, a time at which a characteristic value such as the saturated brightness or a pre-set threshold brightness is attained. The threshold brightness is a value obtained by, for example, multiplying the saturated brightness $I_{max}$, relative to which a TIC is, as shown in (a) of FIG. 7, flat, by an appropriate constant α, for example, 0.8. Otherwise, a mean value $((I_{max}+I_{base})/2)$ of the average brightness before injection $I_{base}$ and the saturated brightness after injection $I_{max}$ may be, as shown in (b) of FIG. 7, adopted. Based on the results of differentiation shown in (c) of FIG. 6, a contrast-medium inflow beginning time ($t_2$) and a saturation time ($t_3$) may be measured, and an intermediate time $((t_3-t_2)/2)$ may be adopted as $t_{TIC}$.

The designation of the threshold brightness and the measurement of the specific change $t_{TIC}$ of the temporal change may be manually performed by an operator, or may be automatically performed by inputting the definition of the threshold brightness to the apparatus in advance. In the manual case, the operator selects a noted region from image data through the input unit, and selects $t_{TIC}$ from a displayed TIC using a pointer or the like on the screen. Since the operator designates the threshold brightness on the basis of an entire image of the TIC of the noted region, designation optimal to a desired region can be achieved.

Figure 8:
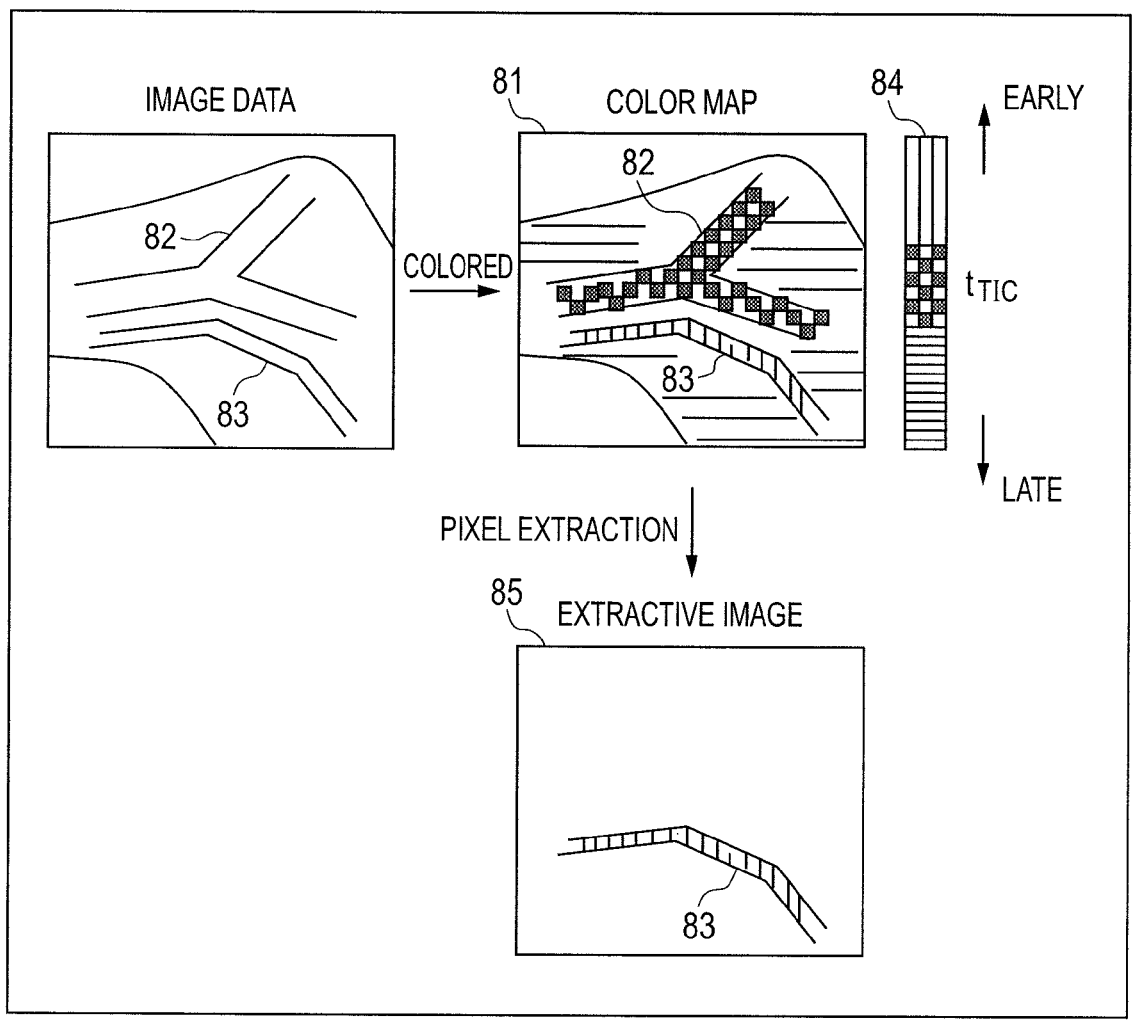
FIG. 8 is a diagram showing a color map and an extractive image in accordance with the embodiment 1.

In process 4, all pixels of image data are differently colored according to measured values of a mapping parameter (that is, information based on a temporal change in brightness of each of the pixels), and a color map 81 is constructed (FIG. 8). FIG. 8 shows an example of the color map 81 with $t_{TIC}$ used as the mapping parameter. A vessel 82, a vessel 83, and a tissue region differently colored based on time differences in $t_{TIC}$ are shown. A color bar 84 indicates association of values of $t_{TIC}$ with shades of a color in the color map 81. A TIC of a region into which a contrast medium does not flow does not reach the threshold brightness, and $t_{TIC}$ of any of pixels in the region is not measured. Such the pixels are automatically discarded or displayed in a predetermined color (black or any other single color), which can be accurately recognized, through pre-designation. Owing to the processing, distinguishing a contrast-enhanced region from a non-contrast enhanced region can be readily achieved not only visually but also as signal processing.

In process 5, information concerning a color map is inputted. On the display 18, items of an artery phase, a portal vein phase, a tissue phase, and others are displayed. An operator freely selects a desired item using the pointer on the screen. As other examples of display items, an item of an abnormal vessel that does not belong to the artery phase, portal vein phase, and tissue phase, and an item of hemodynamics specific to a specific tumor are included.

In process 6, necessary pixels are extracted from a color map according to an item inputted in process 5. The pixels to be extracted are determined based on either association of a mapping parameter with a color in the color map or a temporal change in brightness of each of pixels. For example, if the artery phase is selected in process 5, a region for which $t_{TIC}$ takes on relatively small values is selected based on the color bar 84 shown in FIG. 8, all pixels to which the associated color refers are extracted, and an extractive image 85 showing the artery phase alone is constructed. Pixels representing the dynamics of the artery phase are specifically extracted and visualized, whereby a tumor can be distinguished and the activity thereof can be diagnosed.

Figure 9:
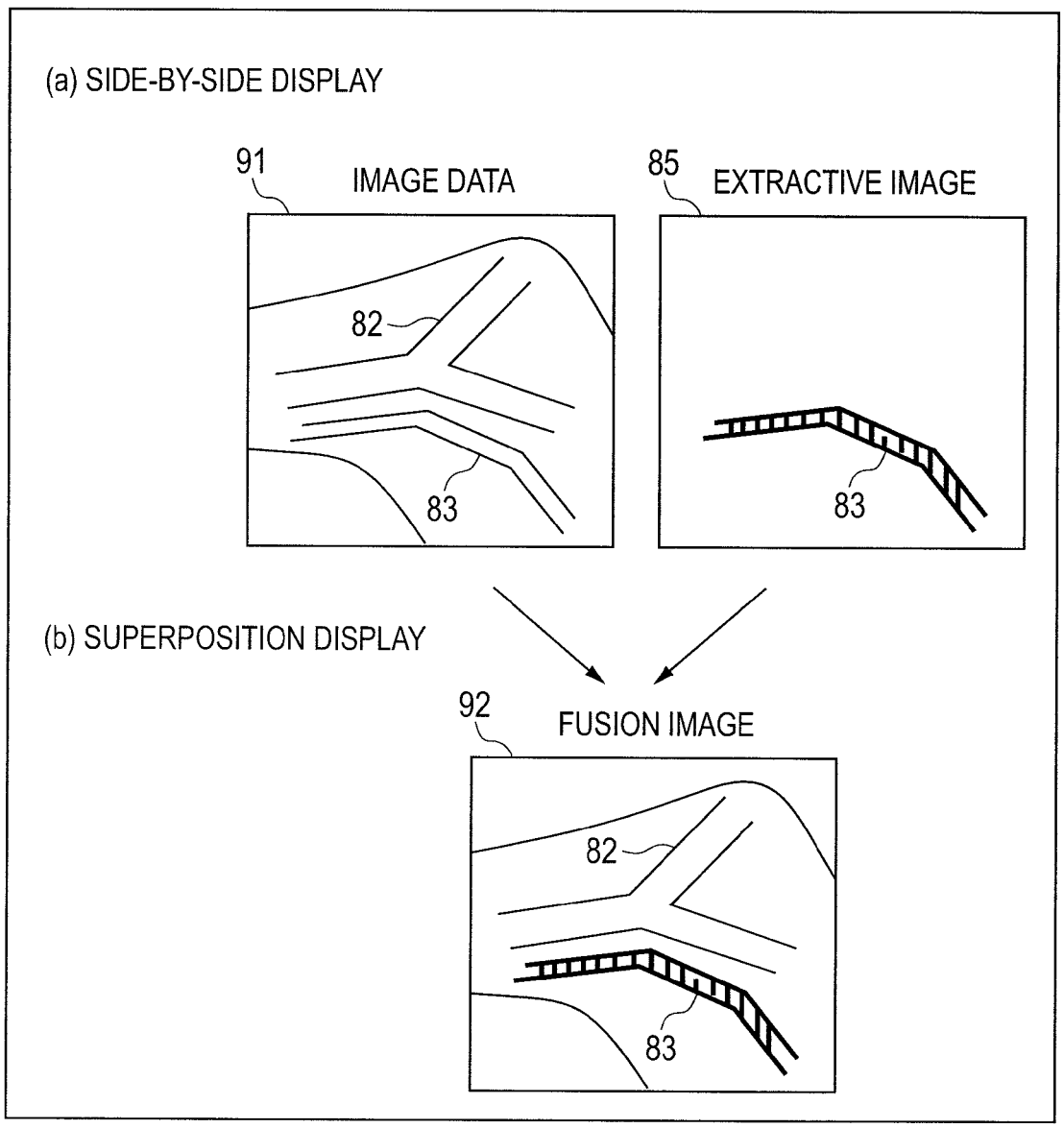
FIG. 9 is a diagram showing a first example of a color map in accordance with the embodiment 1.
Figure 10:
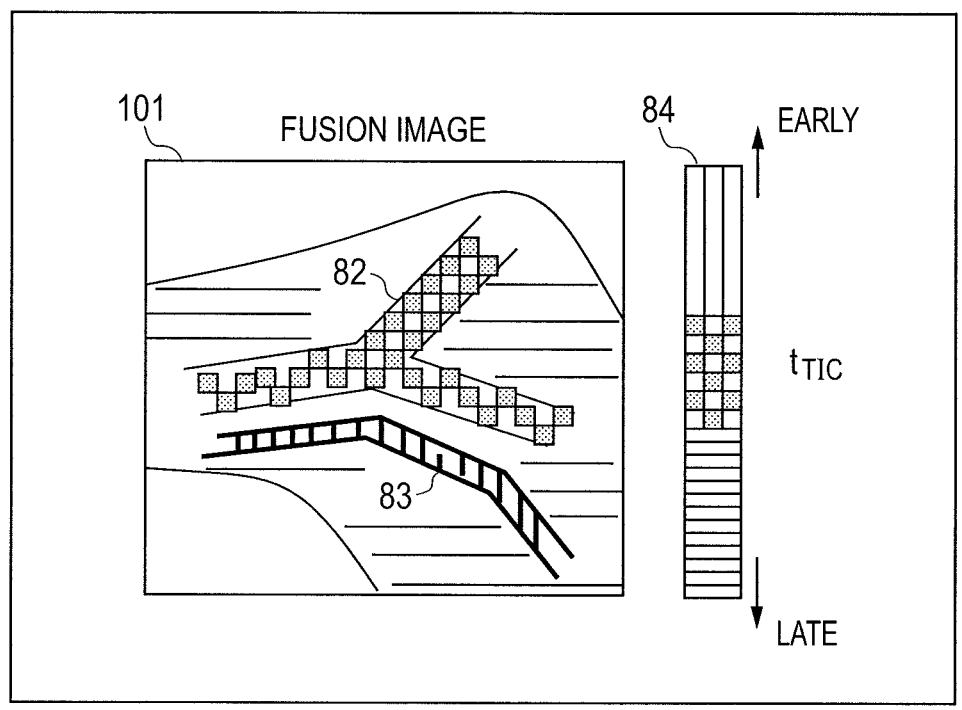
FIG. 10 is a diagram showing a second example of a color map in accordance with the embodiment 1.

In process 7, an image to be displayed is constructed based on the pixels extracted in process 6. FIG. 9 shows an example of a display format. In a display format shown in (a) of FIG. 9, image data 91 read from the scan converter 9 in order to grasp an entire image, and the extractive image 85 having a region equivalent to the artery phase highlighted are displayed side by side. The image data 91 may be a still image or a motion-picture display. Owing to an example 1 (92) of a fusion image having the extractive image 85 superposed on the image data 91, a noted region can be readily identified. Another format is, as shown in FIG. 10, a format of an example 2 (101) of a fusion image having the color map 81 superposed on the image data 91 and having the region of the extractive image highlighted.

The reconstructed color map is displayed on the display 18 (process 8).

In the basic constitution, an operator's manipulation is only to enter a desired display item at the mapping information input unit 16 in process 5. The remaining pieces of processing are all automatically carried out. Therefore, at the same time when the display item is entered, display in the format shown in FIG. 9 or FIG. 10 is achieved. However, in the constitution of the ultrasonic imaging apparatus, the color map 81 constructed in process 4 is preserved in the memory all the time. Information to be displayed can therefore be modified any time. Therefore, the manipulation in process 5 may be omitted. In this case, in process 6, the color map is sent as the extractive image to the color map reconstruction unit 17, and the operator edits the image into a desired image on the basis of the color map displayed on the display 18 according to a technique to be described below.

A technique for modifying or adjusting an evaluation index or a threshold brightness measured in process 4 on the basis of a color map will be described below. When a noted region in a color map is selected using a pointer or the like through the input unit, a TIC of the region and a mapping parameter obtained by the mapping parameter estimation unit 13 are, as show in FIG. 11, displayed on the display 18. Based on the display, an operator finely adjusts the evaluation index or threshold brightness. The contents of adjustment are sent to the color map construction unit 14. After a color map is updated, the color map is re-displayed on the display 18. When fine adjustment of the evaluation index or threshold brightness based on a color map and a TIC of a noted region is performed appropriately, the color map can be optimized in line with an operator's interest. For example, assuming that two vessels which originally exhibit different hemodynamics are decided to bear the same mapping parameter value in the color map, TICs of the two vessels are displayed and the designated threshold brightness is verified. Thus, the validity of the threshold brightness can be decided, and the threshold can be optimally designated while being increased or decreased to be finely adjusted.

Figure 11:
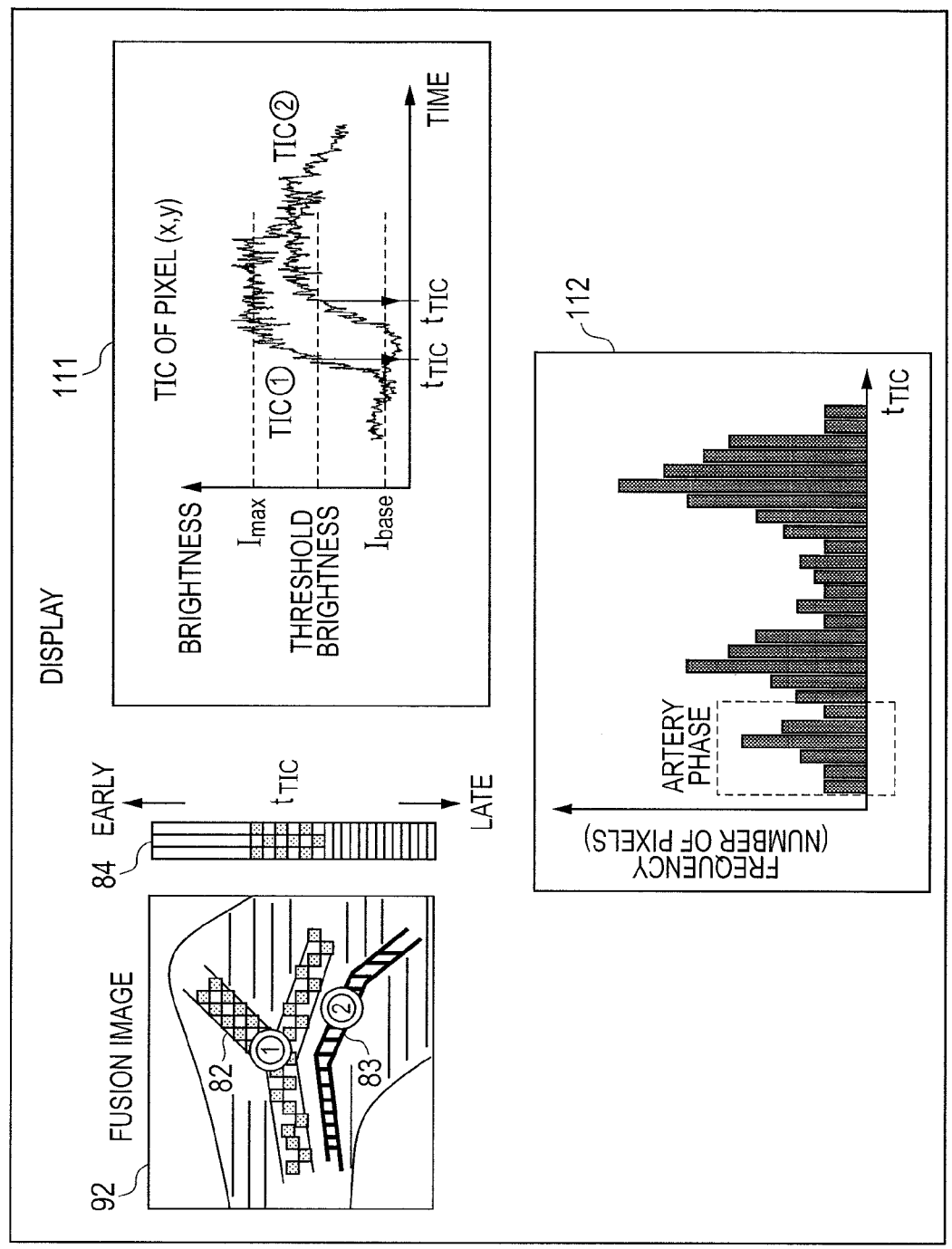
FIG. 11 is a diagram showing an example of a display format, in which a TIC and a frequency distribution table are contained, in accordance with the embodiment 1.

Further, when a frequency distribution display section defined on the display 18 is selected with the pointer, a frequency distribution table having a mapping parameter indicated on the axis of abscissas and the number of pixels, which exhibit each mapping parameter value, indicated on the axis of ordinates is displayed. FIG. 11 shows an example of a display format therefor. In a frequency distribution table 112, the mapping parameter is $t_{TTC}$ and takes on a value that gets larger from left to right. For example, assuming that an operator selects an arbitrary part of the frequency distribution table 112 using the pointer through the input unit, pixels having the associated $t_{TTC}$ are extracted by the color map construction unit 14, and a color map is updated. In addition, the part to be selected may be regarded as a designated region.

By utilizing the frequency distribution table, extraction of a specific region, for example, especially, the hepatic artery is simplified. If an object is the liver, the frequency distribution table 112 shows three peaks associated with the artery phase, portal vein phase, and tissue phase. Since the artery phase and portal vein phase exhibit similar hemodynamics, $t_{TTC}$ values of pixels representing the vessels are close to one another. Therefore, it is hard to optimize a color map for the artery phase using an image, which is differently colored based on $t_{TTC}$ or a specific TIC. Since the frequencies of $t_{TTC}$ of all displayed pixels can be checked owing to the frequency distribution display section, when a designated region is, as shown in FIG. 11, set to the first peak, the artery phase can be more accurately extracted. Incidentally, the frequency distribution table may be displayed as a table of a frequency distribution.

Figure 12:
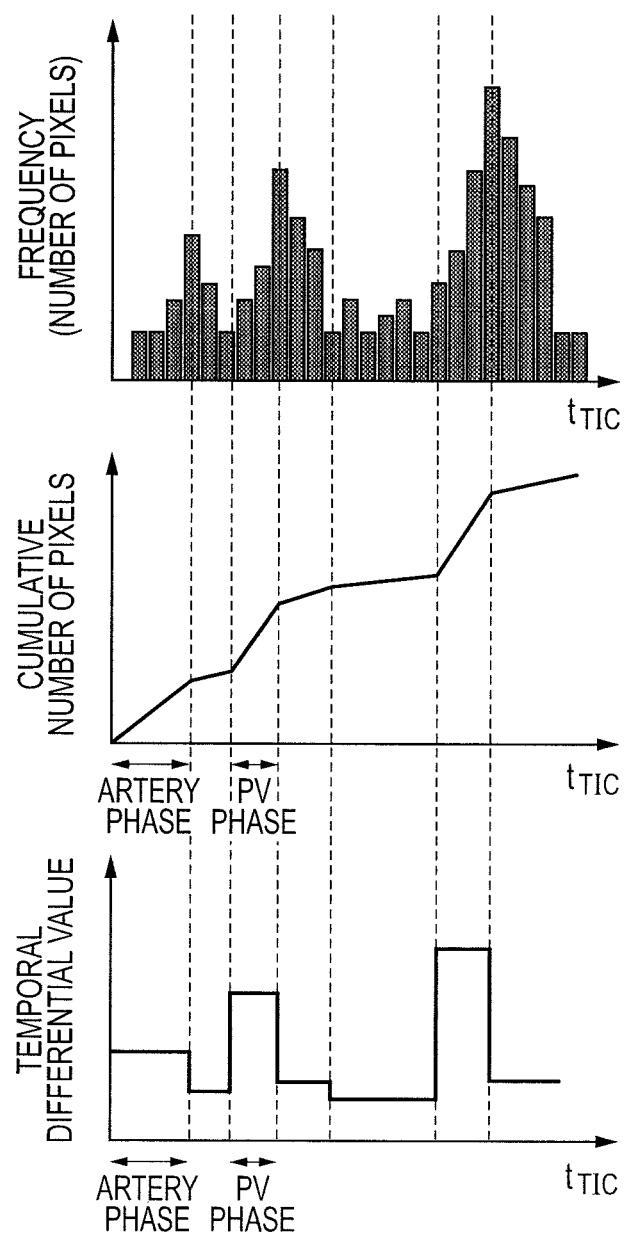
FIG. 12 is a diagram for explaining a technique of identifying an artery phase from a frequency distribution table according to the embodiment 1.

When formation of a frequency distribution table is included in process 3, image display optimized for each contrast-enhancement phase can be achieved at the step of process 4 without the necessity of fine adjustment based on a TIC. In this case, a frequency distribution is displayed on the display, and an operator selects a specific category such as the artery phase. As shown in FIG. 12, $t_{TTC}$ may be plotted on the axis of abscissas, and the cumulative number of pixels may be plotted on the axis of ordinates. Based on the level of a temporal-differentiation value, a time range within which a brightness growth is outstanding, that is, a time range within which inflow of a contrast medium is outstanding can be specified. In process 4, the specific category such as the artery phase may be automatically identified.

The foregoing constitution of the apparatus and the foregoing processing technique are concerned with the contents of processing of discriminating pixels, which represent the artery phase, portal vein phase, or tissue phase, from others, and extracting the pixels. By removing a region, in which the artery phase, portal vein phase, tissue phase, and $t_{TTC}$ cannot be measured, from a color map, a vessel or a tissue exhibiting abnormal contrast-enhancement dynamics may be extracted and displayed while being differently colored in the color map. Even when a region to be designated is, as mentioned above, adjusted using a frequency distribution, a vessel exhibiting dynamics which is intermediate between that of the artery and that of the portal vein can be specifically extracted.

The present technology is a technology of measuring and visualizing a time, at which a characteristic brightness change occurs in a tissue, by utilizing brightness information in image data, but does not restrict image data to be employed. Namely, in the aforesaid constitution of the apparatus, a process of using image data sent from the scan converter 9 has been described. For example, a radiofrequency signal from the receiving beam former 7 may be utilized. The radiofrequency signal that has not been detected by the envelop detector 8 represents directly measured brightness information on a tissue, and a brightness change occurring in the tissue can be extracted from the radiofrequency signal with higher sensitivity than from the image data from the scan converter 9. In addition, an acquisition method for image data is not restricted to any one. Image data constructed based on a receiving signal in the same frequency band as an ultrasonic transmitting signal does may be employed. In addition, image data obtained by utilizing a property of a contrast medium exhibiting a non-linear behavior, and utilizing a receiving signal in a different frequency band from a transmitting signal may be utilized.

Owing to the aforesaid constitution, even when a contrast medium is used once, the artery phase, portal vein phase, and tissue phase can be identified, that is, contrast-enhancement phases of a subject can be differentiated.

A description has been made of the embodiment. The present invention is not limited to the embodiment. It will be apparent to a person with ordinary skill in the art that various modifications and alterations can be made within the spirit of the present invention and the scope of appended Claims.

The invention claimed is:

1. An ultrasonic imaging apparatus comprising:
   a transducer that transmits or receives ultrasonic waves to or from a subject;
   an image data production unit configured to produce a plurality of image data items on the basis of a plurality of receiving signals due to the transducer;
   a frame memory configured to preserve the image data items;
   a temporal change measurement unit configured to measure a temporal change in brightness of each of pixels of image data;
   an image construction unit configured to construct a color map on the basis of the results of measurement by the temporal change measurement unit;
   an input unit configured to input display-item information concerning the color map; and
   a pixel detection unit configured to extract pixels from the color map so as to construct an extractive image;
   wherein the ultrasonic imaging apparatus further comprising:
   a mapping parameter estimation unit configured to measure a saturated brightness($I_{max}$) of the contrast medium, and an average brightness ($I_{base}$) before injection per each of pixels on the basis of the temporal change measured by the temporal change measurement unit, and configured to calculate a mapping parameter on the basis of the measured temporal change,
   wherein: the image construction unit configured to construct the color map on the basis of the mapping parameter.

2. The ultrasonic imaging apparatus according to claim 1, further comprising a color map reconstruction unit configured to reconstruct a color map using the extractive image and image data, and a display that displays the color map.

3. The ultrasonic imaging apparatus according to claim 2, wherein the display includes a frequency distribution display section in which the number of pixels associated with a specific change time of the temporal change is displayed.

4. The ultrasonic imaging apparatus according to claim 2, wherein the display displays a specific change time of the temporal change in a region an operator selects, and a mapping parameter.

5. The ultrasonic imaging apparatus according to claim 2, wherein the color map reconstruction unit configured to reconstruct as the color map an image that has the image data, color map, and extractive image combined arbitrarily.

6. The ultrasonic imaging apparatus according to claim 2, wherein the color map reconstruction unit configured to reconstruct as the color map any of an image that has the differently colored color map translucently superposed on image data displayed as a motion picture, an image that has the differently colored extractive image translucently superposed on the image data displayed as a motion picture, and an image that has a specific region highlighted.

7. The ultrasonic imaging apparatus according to claim 2, further comprising a mapping parameter estimation unit configured to calculate a mapping parameter on the basis of a measured temporal change, wherein:
the input unit configured to receive a selective input of a region in a color map; and
the display displays the temporal change in brightness of each pixel in the region selected based on the selective input, and the mapping parameter.

8. The ultrasonic imaging apparatus according to claim 1, further comprising a motion correction unit configured to compensate an effect of a body motion on image data preserved in the frame memory.

9. The ultrasonic imaging apparatus according to claim 1, wherein a specific change time of the temporal change is measured based on the brightness of a pixel.

10. The ultrasonic imaging apparatus according to claim 1, wherein the image construction unit configured to construct as the color map an image that has the temporal change in brightness of each pixel discriminated in color.

11. The ultrasonic imaging apparatus according to claim 1, wherein contract-enhancement phases of the subject are differentiated based on a differential value of the temporal change in brightness of each pixel.

12. The ultrasonic imaging apparatus according to claim 1, wherein the input unit displays display items, and receives as an input an operator's selection of any of the display items.

13. The ultrasonic imaging apparatus according to claim 1, wherein the pixel detection unit configured to determine pixels to be extracted according to either association of the mapping parameter with a color in the color map or the temporal change in brightness of each pixel.

14. The ultrasonic imaging apparatus according to claim 1, wherein assuming that an equation expressing the temporal change in brightness of each pixel is $I=I_{max}(1-\exp(-\beta t))$, the mapping parameter is any of a saturated brightness ($I_{max}$) attained when a flow rate of a contrast medium is saturated, a value ($\beta$) representing an acceleration of the contrast-medium inflow rate, and a time at which a specific brightness value is attained.

15. An ultrasonic imaging apparatus comprising:
a transducer that transmits or receives ultrasonic waves to or from a subject, an object region of which is enhanced by a contrast medium;
an image data production unit configured to produce a plurality of image data items on the basis of a plurality of receiving signals due to the transducer;
a frame memory that preserves the image data items;
a temporal change measurement unit configured to measure a temporal change in brightness of each of pixels of image data;
a mapping parameter estimation unit configured to measure a saturated brightness ($I_{max}$) of the contrast medium, and an average brightness ($I_{base}$) before injection per each of pixels on the basis of the temporal change measured by the temporal change measurement unit, and calculates a mapping parameter indicating the temporal change in brightness, and a differential value of the mapping parameter on the basis of the saturated brightness ($I_{max}$) and the average brightness ($I_{base}$);
an image construction configured to construct a color map on the basis of the mapping parameter, the color map discriminating the temporal change in brightness of each of pixels in color;
an input configured to input display-item information concerning the color map; and
a pixel detection unit configured to extract pixels from the color map so as to construct an extractive image,
wherein contract-enhancement phases of the subject are differentiate based on the differential value of the mapping parameter calculated by the mapping parameter estimation unit.

* * * * *